US005523443A

United States Patent [19]
Gaglani

[11] Patent Number: 5,523,443
[45] Date of Patent: Jun. 4, 1996

[54] DUAL CURING CONFORMAL COATINGS

[75] Inventor: Kamlesh Gaglani, South Plainfield, N.J.

[73] Assignee: CasChem, Inc., Bayonne, N.J.

[21] Appl. No.: 134,123

[22] Filed: Oct. 8, 1993

Related U.S. Application Data

[63] Continuation-in-part of Ser. No. 960,042, Oct. 13, 1992.

[51] Int. Cl.$^6$ ........................................... C07F 7/10
[52] U.S. Cl. ........................... 556/421; 556/414; 556/420
[58] Field of Search ................... 556/414, 420, 556/421

[56] References Cited

U.S. PATENT DOCUMENTS

| | | | |
|---|---|---|---|
| 3,179,622 | 4/1965 | Haluska | 556/414 X |
| 3,179,713 | 4/1965 | Brown | 556/414 X |
| 3,426,057 | 2/1969 | Kanner | 556/414 |
| 3,502,704 | 3/1970 | McKellar | 556/414 |
| 3,895,043 | 7/1975 | Wagner et al. | 556/421 |
| 3,903,052 | 9/1975 | Wagner et al. | 556/420 X |
| 4,031,120 | 6/1977 | Gervase | 556/414 |
| 4,088,670 | 5/1978 | Bargain et al. | 556/420 X |
| 4,650,835 | 3/1987 | Eck et al. | 556/421 X |
| 5,120,812 | 6/1992 | O'Lenick | 556/414 X |
| 5,166,383 | 11/1992 | Parrinello et al. | 556/414 |

*Primary Examiner*—Paul F. Shaver
*Attorney, Agent, or Firm*—Pennie & Edmonds

[57] ABSTRACT

Ultraviolet curable polymerizable systems having a built-in secondary curing mechanism are disclosed. The polymerizable coating system is a one component system comprising at least one alkoxysilyl-urethane-acrylate or methacrylate, an acrylate or methacrylate or vinyl ether diluent. The coating systems may include a polymerization initiator of the cationic or free radical photoinitiator type, and a metal catalyst. The coating system is UV curable, and also possesses an additional cure mechanism.

15 Claims, No Drawings

DUAL CURING CONFORMAL COATINGS

This is a Continuation-In-Part of Ser. No. 07/960,042 filed Oct. 13, 1992, now allowed.

FIELD OF THE INVENTION

The invention generally relates to dual cure conformal coating formulations. More particularly, the invention relates to resins for use in dual cure conformal coating applications.

BACKGROUND OF THE INVENTION

Conformal coatings provide a protective covering over automobile, aerospace and military electronic printed circuit boards. These coatings protect sensitive electronic components from corrosion of solder joints, fluids, hydraulic fluids, dirt, dust, moisture, mildew, physical abrasion or damage from handling and short circuits. Coated boards therefore can be protected from environmental, mechanical and electrical interferences.

The conformal coatings of the prior art have utilized chemistries such as acrylic, polyurethane, silicone, polyimide, epoxies, and parylene. These formulations, however, have suffered from several disadvantages. For example, conformal coatings formed from polyurethanes, acrylics, epoxy and silicone are two part systems which must be mixed prior to application and require continuous monitoring and solvent additions to control viscosity. These formulations usually also require long drying/curing times and release large amounts of volatile organic compounds (VOC) during curing.

Conformal coating systems based on acrylics are excellent from a production standpoint. However, acrylic coatings typically are formed by solvent evaporation which generates large amounts of VOC. Conventional acrylic coatings also are soluble in chlorinated solvents such as tricholorethane or methylene chloride.

Conformal coatings based on polyurethanes are available as either single or two-component systems. Polyurethane coatings offer excellent humidity and chemical resistance and good dielectric properties. Single-component urethanes are relatively easy to apply and exhibit relatively long working pot life. However, single-component polyurethanes typically require a curing time of three to ten days at room temperature to reach optimum physical characteristics. Two-component polyurethanes typically achieve optimum cure at elevated temperatures within one to three hours, but exhibit relatively short working pot life.

Surface preparation of substrates prior to application of polyurethane based coatings is also important, since even minute quantities of moisture on a substrate board could produce blistering under humid conditions. Blisters, in turn, may lead to electrical failures and mandate costly rework. Polyurethane coatings are insoluble in most common solvents, which is a drawback to rework. Thus, replacement of a component on a polyurethane coated board requires a corrosive stripper to remove effectively all traces of the polyurethane film. However, extreme caution must be exercised when such a stripper is used, because the stripper also may corrode metallic surfaces on the board.

Epoxy resin systems also have been employed for conformal coating of printed circuit boards. Epoxy resins are available as two component systems only. Epoxy resin coatings provide good humidity resistance and high abrasive and chemical resistance. However, epoxy resins are virtually impossible to remove chemically for rework because any stripper that will attack the coating also will attack the epoxy-glass of the printed circuit board as well. Thus, the only effective way to repair an epoxy resin coated board is to burn through the epoxy coating with a hot knife or soldering iron. However, burning introduces a cosmetic defect which is unacceptable to many consumers. Moreover, epoxy resins shrink somewhat during cure. Accordingly, a buffer material must be placed around fragile electronic components to prevent fracturing from shrinkage. Curing of epoxy systems can be accomplished in one to three hours at elevated temperature, or four to seven days at room temperature. Epoxy resins exhibit a relatively short working pot life which is an additional disadvantage.

Silicone resins have been employed for conformal coatings. Silicone resin coatings provide high humidity and corrosion resistance along with high temperature resistance which makes silicone resins preferred for coating printed circuit assemblies that contain high heat-dissipating components such as power resistors. However, silicone resins are relatively thick and therefore difficult to apply. Moreover, silicone resins require a relatively long cure time, and repairability is difficult. The only effective way to repair a silicone resin coated circuit board is to mechanically remove the coating.

The prior art has employed polyimides for conformal coating circuit boards. Polyimide coatings provide high-temperature, moisture and chemical resistance over extended periods of time. However, polyimide coatings require high temperature cure (one to three hours at 200° to 250° C.) which can damage heat sensitive electronic components. Also, since polyimides are high-temperature, moisture and chemical resistant, the only effective way to repair a polyimide coated board is to mechanically remove the coating.

Several of these disadvantages have been addressed by use of ultraviolet (UV) curable conformal coatings. The UV curable coatings of the art are one part systems which usually are devoid of solvents to thereby reduce or eliminate the (VOC) emission. These systems are cured rapidly by UV to provide tack-free coatings via free-radical or cationic polymerization. This enables immediate handling of the coated articles for further processing, storage or shipping. Moreover, use of UV curable coatings reduces overall processing time and energy costs as compared to thermally cured coatings.

The UV cured systems of the art have been useful for coating flat surfaces. However, printed circuit boards which bear electronic components tend to be oddly configured. These odd configurations cause shadow areas which cannot be reached by UV radiation. The coated portions in these shadow areas therefore remain wet and cannot be handled immediately. Secondary cure mechanisms such as heat have been employed to polymerize these shadowed areas. The drawback of heat induced secondary curing, however, is that temperatures of up to 100° C. are required to cure the shadowed areas. These temperatures can adversely affect sensitive electronic components.

A need therefore exists for conformal coatings which overcomes the above drawbacks. I therefore have developed a novel, dual-curing conformal coating composition that is a solvent-free low viscosity liquid that rapidly cures into a tack-free polymer when exposed to UV light. Those portions of the coatings which are not cured by UV can be cured in less than 24 hours by a moisture cure component provided in the coating formulation.

SUMMARY OF THE INVENTION

Ultraviolet curable polymerizable coating systems having a built-in secondary moisture curing mechanism are disclosed. The polymerizable coating system is a one component system comprising the reaction product of an organic polyisocyanate, an acrylate substituted polyol, and an alkoxysilane substituted amine. These reaction products have the composition of either one of Formulae (I), (II) or (III):

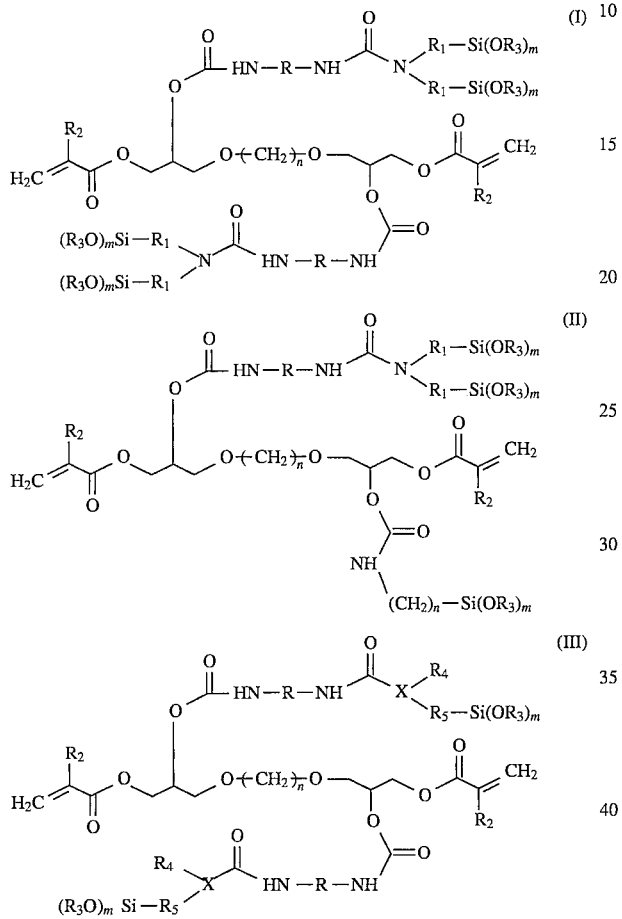

In each of Formulae (I) and (II), R can be an alkyl radical of $C_2$–$C_{12}$; —$(CH_2)_{2n}$ where n=1–6, preferably 6; cycloalkyl substituted alkyl such as dicyclohexyl methane and the like; aryl substituted alkyl such as stilbene, biphenyl methane 2,4-cumene and the like, aryl such as diphenyl, anthracene, naphthalene and the like; halo substituted aryl such as 4-chloro-1,3-phenylene, 4-bromo-1,3-phenylene, and the like; alkoxy phenylene such as 4-ethoxy-1,3-phenyl and the like; aryl ethers such as diphenyl ether and the like; alkyl substituted phenylene such as 2,4-dimethyl- 1,3-phenylene, 4,6-dimethyl-1,3-phenylene and the like; polymethylenes such as tetramethylene, pentamethylene, hexamethylene, and cycloalkylenes such as cyclohexyl, benzofuran, amyl benzene; aryl such as phenyl, Biphenyl, 1,5-naphtahalene, antracene and the like; alkoxy substituted aryl such as 4-methoxy- 1,3-phenylene, and the like; alkyl substituted aryl such as 5,6-dimethyl-1,3-phenylene, 2,4,-dimethyl-1,3-phenylene, 4,6-dimethyl-1,3-phenylene, and the like; aryl ether such as 2,4-diphenyl ether and the like; alkoxy substituted aryl alkyl such as 3,3'-dimethoxy- 4,4'-phenyl methane, and the like; alkylene such as tetramethylene, pentamethylene, hexamethylene, and the like and hetero chains such as —R'—[O(CH$_2$)$_x$—O]$_y$—R' where

R'=R as defined above, x=2–10 and y=1–10;

$R_1$ represents a linear or branched primary, secondary or tertiary alkyl radical substituted with an alkoxy silane, preferably a trialkoxy silane moiety. Examples of alkyl radicals which may be employed as $R_1$ have from 2 to 12 carbon atoms such as ethyl, propyl, butyl, pentyl, hexyl, heptyl, octyl, 2-dodecyl, 3-dodecyl, 2,3-dimethyl decyl, 2-ethyl decyl, 2,5-dimethyldecyl, n-penta decyl, 2-hexa decyl, n-hepta decyl, 2-hepta decyl, 2 methyl-2-hepta decyl, 2-ethyl-2-hexa decyl, n-nona decyl, n-eicosyl, sec-eicosyl, n-hexaeicosyl, and n-docosyl;

$R_2$ is at least one of H, —$CH_3$, —$C_2H_5$, $C_3H_7$, $C_4H_8$;

$R_3$ is at least one of —$CH_3$, —$C_2H_5$;

and n is 2–20.

In Forumla (III):

X is any of O, N and S, with the proviso that when X is either O or S, $R_4$ is not present;

n is an integer from 2 to 20;

m is an integer from 1–3;

R and $R_2$ are the same as in Formulae (I) and (II);

$R_3$ is the same as Formulae (I) and (II);

$R_4$ can be any of $R_1$ as in formula (I) and (II), $C_1$–$C_{25}$ branched or straight alkyl such as methyl, ethyl, propyl, butyl, pentyl, hexyl, heptyl, octyl, 2-dodecyl, 3-dodecyl, 2,3-dimethyl decyl, 2-ethyl decyl, 2,5-dimethyldecyl, n-penta decyl, 2-hexa decyl, n-hepta decyl, 2-hepta decyl, 2 methyl-2-hepta decyl, 2-ethyl-2-hexa decyl, n-nona decyl, n-eicosyl, sec-eicosyl, n-hexaeicosyl, and n-docosyl; aryl such as phenyl, biphenyl, 1,5-naphthalene, anthracene, and the like; substituted aryl such as 4-methoxy-1,3-phenylene, 4-chloro-1,3-phenylene, 4-bromo-1,3-phenylene and the like; and $R_5$—Si—$(OR_3)_m$ where m=1–3.

$R_5$ can be any of formula (6) or (7)

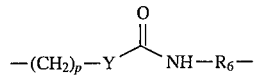

and,

where p is an integer from 2 to 25; Y is any of O, S or N

In Formulae (6) and (7) $R_6$ is any of $C_2$–$C_{25}$ straight and branched alkyl such as ethyl, propyl, butyl, pentyl, hexyl, heptyl, octyl, 2-dodecyl, 3-dodecyl, 2,3-dimethyl decyl, 2-ethyl decyl, 2,5-dimethyldecyl, n-penta decyl, 2-hexa decyl, n-hepta decyl, 2-hepta decyl, 2 methyl-2-hepta decyl, 2-ethyl- 2-hexa decyl, n-nona decyl, n-eicosyl, sec-eicosyl, n-hexaeicosyl, and n-docosyl; aryl such as phenyl, biphenyl, 1,5-naphthalene, anthracene, and the like; substituted aryl such as 4-methoxy-1,3-phenylene, 4-chloro-1,3-phenylene, 4-bromo-1,3-phenylene and the like.

$R_7$ is any of $C_1$–$C_{25}$ branched or straight alkyl such as methyl, ethyl, propyl, butyl, pentyl, hexyl, heptyl, octyl, 2-dodecyl, 3-dodecyl, 2,3-dimethyl decyl, 2-ethyl decyl, 2,5-dimethyldecyl, n-penta decyl, 2-hexa decyl, n-hepta decyl, 2-hepta decyl, 2-methyl-2-hepta decyl, 2-ethyl-2- hexa decyl, n-nona decyl, n-eicosyl, sec-eicosyl, n-hexaeicosyl, and n-docosyl; aryl such as phenyl, biphenyl, 1,5-naphthalene, anthracene, and the like and substituted aryl such as 4-methoxy-1,3-phenylene, 4-chloro- 1,3-phenylene, 4-bromo-1,3-phenylene and the like.

In resin compositions which include reaction products corresponding to those of Formulae (I), (II) and (III), a catalyst may be included to increase the rate of moisture curing, and a photoinitiator may be included to increase the rate of UV curing. Surfactants to enhance the flow characteristics of the composition also can be included.

A particular feature and advantage of the invention is that UV radiation produces extremely rapid, dry-to-the-touch curing of exposed areas of the coating to permit immediate handling of the coated products. The rapid drying also acts to retain the shape of the coating which might otherwise sag and creep. The secondary moisture curing provides substantially complete cure of unexposed (shadow) areas of the coating under conditions of ambient temperature and humidity.

The term "dry-to-the-touch" as used herein with reference to physical properties of the materials, is to be understood as referring to such properties as they exist under conditions as may be specified. For example, the term "dry-to-the-touch" is to be understood as referring respectively to physical states wherein a material is resistant to change in shape and is without free surface moisture or surface tackiness.

The UV curable coating formulations of the present invention primarily are intended for application to electronic circuit boards. However, due to the configuration of many circuit boards, there are areas of the board that are in the shadow of other components such that they cannot be cured by UV light. To overcome this deficiency, a second curing mechanism has been built into the coating system.

The radiation curable resin formulations of the invention may be used as coatings on various substrates including, but not limited to, glass, ceramic, concrete, metal, plastic, brick, paper, cardboard, wood, resilient flooring, e.g., vinyl and vinyl-asbestos tile and vinyl sheet goods, and the like. Coating thicknesses may range from 0.25 to 5 mils. The conformal coatings of the invention are especially useful to protect printed circuit boards that have sensitive electronic components from corrosion due to fluids, hydraulic fluids, dirt, dust, moisture, mildew, abrasion, and damage from handling. For a fuller understanding of the nature and objects of the present invention, reference is made to the following detailed description of the invention taken in connection with the accompanying, non-limiting examples.

DETAILED DESCRIPTION OF THE INVENTION

Generally, the dual curing resin compositions of the invention include a resin oligomer of either one of Formula (I), (II) or (III), acrylate monomers, photoinitiators, catalysts, and surfactants. A typical formulation includes 40–80% resin oligomer of Formula (I), (II) or (III), preferably 45% to 75%; 20–60% monomer acrylates, preferably 25 to 55%, most preferably 25%; 2–8% photoinitiator, preferably 2 to 4%, most preferably 3%; 1–3% catalyst, preferably 1–2%, most preferably 1%; and 0–2% of a surfactant, preferably 0.5–1%. The resulting compositions can be cured by ultraviolet (UV) radiation, optionally together with exposure to moisture in air.

The resin oligomers of the invention which may be used to provide the conformal coating formulations of the invention may be formed by methods known to one skilled in the art. However, several methods in accordance with the invention enable formation of the oligomers of Formulae (I), (II) or (III) from commercially available reactants. In a first method, resin oligomers according to Formulae (I), or (II), as well as oligomers of Formula (III) where X is nitrogen, are formed by reacting a urea derivative and an acrylate substituted diol. Typically, the resin oligomer is made by reacting 1–6 moles of urea derivative with 1–3 moles of the acrylate substituted diol. The urea derivative typically is made by reacting 1–6 moles of a diisocyanate with 1–3 moles of amine. The amine employed can be a secondary amine substituted with alkyl groups substituted with an alkoxysilane moiety, preferably a trialkoxy silane moiety.

In an alternative method of forming the resin oligomers of the invention, the urea derivative produced in the first method described above is reacted with both an isocyanate and a diol disubstituted with acrylate or methacrylate moieties. The reaction ratio of the equivalent weights of diol to isocyanate can be 1 to 3, preferably 1 to 2.

Oligomers of Formula (III), where X is oxygen, can be formed by reacting a polyol with a polyisocyanate and an alcohol. Oligomers of Formula (III), where X is sulpher, can be formed by reacting a polyol with a polyisocyanate and a thiol. Typically 2–6 moles of polyol are reacted with 1–3 moles of polyisocyanate and 1–3 moles of alcohol or thiol to obtain the desired oligomer.

As discussed above, resin oligomers of Formula (I) are produced by reacting a urea derivative and an acrylate substituted diol. The urea derivatives employed in this reaction correspond to Formula (1):

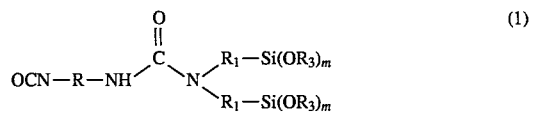

(1)

where R represents an alkyl radical of $C_2$–$C_{12}$; —$(CH_2)_{2n}$ where n=1–6, preferably 6; cycloalkyl substituted alkyl such as dicyclohexyl methane and the like; aryl substituted alkyl such as stilbene, biphenyl methane 2,4-cumene and the like; aryl such as diphenyl, anthracene, naphthalene and the like; halo substituted aryl such as 4-chloro-1,3-phenylene, 4-bromo-1,3-phenylene, and the like; alkoxy phenylene such as 4-ethoxy-1,3-phenyl and the like; aryl ethers such as diphenyl ether and the like; alkyl substituted phenylene such as 2,4-dimethyl-1,3-phenylene, 4,6-dimethyl- 1,3-phenylene and the like; polymethylenes such as tetramethylene, pentamethylene, hexamethylene, and cycloalkylenes such as cyclohexyl, benzofuran, amyl benzene; aryl such as phenyl, Biphenyl, 1,5-naphtahalene, antracene and the like; alkoxy substituted aryl such as 4-methoxy-1,3-phenylene, and the like; alkyl substituted aryl such as 5,6-dimethyl- 1,3-phenylene, 2,4,-dimethyl-1,3-phenylene, 4,6-dimethyl-1,3-phenylene, and the like; aryl ether such as 2,4-diphenyl ether and the like; alkoxy substituted aryl alkyl such as 3,3'-dimethoxy-4,4'-phenyl methane, and the like; alkylene such as tetramethylene, pentamethylene, hexamethylene, and the like, and hetero chains such as

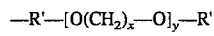

where

R'=R as defined above, x=2–10 and y= 1–10;

$R_1$ represents a linear or branched primary, secondary or tertiary alkyl radical substituted with an alkoxy silane, preferably a trialkoxy silane moiety. Examples of alkyl radicals which may be employed as $R_1$ have from 2 to 12 carbon atoms such as ethyl, propyl, butyl, pentyl, hexyl, heptyl, octyl, 2-dodecyl, 3-dodecyl, 2,3-dimethyl decyl, 2-ethyl decyl, 2,5-dimethyldecyl, n-penta decyl, 2-hexa decyl, n-hepta decyl, 2-hepta decyl, 2 methyl-2-hepta decyl, 2-ethyl-2-hexa decyl, n-nona decyl, n-eicosyl, sec-eicosyl, n-hexaeicosyl, and n-docosyl; Preferably, R is either dicyclohexylmethane or hexamethylene, most preferably dicyclohexylmethane. Preferably, $R_1$ is a linear or branched primary alkyl or a linear secondary alkyl radical having from 2 to 4 carbons such as ethyl, propyl, or butyl, most preferably propyl. More preferably, $R_1$ is a linear or branched primary alkyl group having from 2 to 3, most preferably three carbon atoms; both $R_1$ substituents may be the same or different. $R_3$ may be any one of linear or branched primary, secondary or tertiary alkyl radicals having 2 to 4 carbon atoms; both $R_3$ substituents may be the same or different. Examples of alkyl radicals which may be employed as $R_3$ include $C_4H_8$, preferably $C_2H_4$, most preferably $C_3H_6$.

The urea derivatives of Formula (1) are formed by reacting an organic polyisocyanate with a secondary amine or primary amine. Of these polyisocyanates, diisocyanates are preferred due to cost and availability. Typical diisocyanates which may be used in synthesis of the urea derivatives employed to provide the resin oligomers of the invention include but are not limited to 1,5-naphthalene diisocyanate; cumene-2,4-diisocyanate; 4-methoxy-1,3-phenylene diisocyanate; 4-chloro-1,3-phenylene diisocyanate; 4-bromo-1,3-phenylene diisocyanate; 4-ethoxy-1,3-phenylene diisocyanate; 2,4'-diisocyanato diphenyl ether; 5,6-dimethyl-1,3-phenylene diisocyanate; 2,4-dimethyl-1,3-phenylene diisocyanate; 4,4'-diisocyanato diphenyl ether; benzidine diisocyanate; 4,6-dimethyl-1,3-phenylene diisocyanate; 9,10-anthracene diisocyanate; 4,4'-diisocyanato diphenyl; 2,4-diisocyanatostilbene, 3,3'-dimethoxy-4,4'-diisocyanato phenyl methane; 3,3'-dimethoxy-4,4'-diisocyanato diphenyl; 1,4-anthracene diisocyanate; 2,5-fluorene diisocyanate; 1,8-naphthalene diisocyanate, 2,6-diisocyanato benzfuran; amyl benzene- 2,4-diisocyanate; polymethylene diisocyanates such as tetramethylene diisocyanate, pentamethylene diisocyanate, hexamethylene diisocyanate and the like; cycloaklylene diisocyanates such as cyclohexylene- 1,4-diisocyanate; 4,4'-methylene bis(cyclohexyl isocyanate); isophorone diisocyanate; hetero chain diisocyanates such as OCN—R—[(OCCH$_2$)$_m$—O]$_n$R—NCO when R is as defined above, m=2–10, and n=1–10.

Useful secondary amines which may be employed to react with the above diisocyanates to form the urea derivatives (1) employed to produce the resin oligomers of Formulae (I) and (II), as well as the oligomers of Formula (III) where X is N, include amino compounds of formula (2)

where m=1–3, $R_1$ is a linear or branched primary, secondary or tertiary alkyl radical substituted with an alkoxy silane, preferably a trialkoxy silane moiety. Examples of alkyl radicals which may be employed as R have from 2 to 12 carbon atoms such as ethyl, propyl, butyl, pentyl, hexyl, heptyl, octyl, dodecyl, 2-dodecyl, 3-dodecyl, 2,3-dimethyl decyl, 2-ethyl decyl, 2,5-dimethyldecyl, n-penta decyl, 2-hexadecyl, n-heptadecyl, 2-heptadecyl, 2 methyl-2-hepta decyl, 2-ethyl-2-hexadecyl, n-nonadecyl, n-eicosyl, sec-eicosyl, n-heneicosyl, and n-docosyl. Preferably $R_1$ is a linear or branched primary alkyl or a linear secondary alkyl radical having from 2 to 4 carbons. Most preferably, $R_1$ is a linear or branched primary alkyl group having from 2 to 3 carbon atoms; both $R_1$ substituents may be the same or different. $R_3$ may be any one of linear or branched primary, secondary or tertiary alkyl radicals having 2 to 4 carbon atoms. Examples of alkyl radicals which may be employed as $R_3$ include $C_4H_8$, $C_2H_4$, $C_3H_6$. Typically, 1–6 moles of diisocyanates can be reacted with 1–3 moles of the amine to provide urea derivatives which may be employed in the invention.

A urea derivative of Formula (1) is reacted with an acrylate substituted diol of Formula (3)

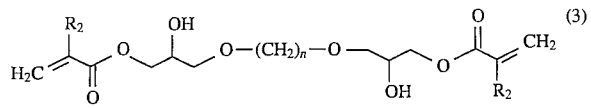

where $R_2$ is any of H, —CH$_3$, —C$_2$H$_5$, or $C_1$–$C_4$ alkyl, and n=2–20 to provide the resin oligomers of Formula (I) defined above.

The resin oligomers of the Formula (II) are formed by reacting a urea derivative of the above Formula (1) with:

(a) an isocyanate of Formula (4)

where i=2–20, preferably 6; j=1–3, preferably 3; $R_4$ is $C_1$–$C_4$ alkyl, preferably CH$_3$ or C$_2$H$_5$; and (b) an acrylate substituted diol of Formula (3). Non-limiting examples of isocyanate reactants which may be employed include 3-isocyanatopropyl trimethoxysilane; 3-isocyanatopropyl triethoxysilane; 4-isocyanatobutyl trimethoxysilane; 4-isocyanato butyl triethoxysilane; 5-isocyanatopentyltrimethoxysilane; 5-isocyanato pentyltriethoxysilane; 6-isocyanatohexyl trimethoxysilane; and 6-isocyanato hexyl triethoxysilane, preferably, 3-isocyanatopropyl triethoxysilane and 3-isocyanatopropyl trimethoxysilane; most preferably 3-isocyanatopropyl trimethoxysilane.

Resin Oligomers according to formula (III) can be formed using several different synthesis routes depending on whether X is nitrogen, oxygen or sulphur. When X is nitrogen, oligomers of formula (III) are produced by reacting a polyol, typically an acrylate substituted diol, with a urea derivative of formula (5).

Urea derivitives of formula (5) useful in making oligomers of formula (III) where X is nitrogen have the general formula:

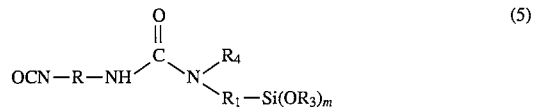

where R and $R_3$ are as defined in Formula (I) and (II); $R_4$ is any of $R_1$ as defined above in formula (III), $C_1$–$C_{25}$ branched or straight alkyl such as ethyl, propyl, butyl, pentyl, hexyl, heptyl, octyl, 2-dodecyl, 3-dodecyl, 2,3-dimethyl decyl, 2-ethyl decyl, 2,5-dimethyldecyl, n-penta decyl, 2-hexa decyl, n-hepta decyl, 2-hepta decyl, 2 methyl-2-hepta decyl, 2-ethyl- 2-hexa decyl, n-nona decyl, n-eicosyl, sec-eicosyl, n-hexaeicosyl, and n-docosyl; aryl such as phenyl, biphenyl, 1,5-naphthalene, anthracene, and the like, substituted aryl 5,6-dimethyl-1,3-phenylene, 2,4-dimethyl- 1,3-phenylene, 4-ethoxy-1,3-phenylene, 4-chloro- 1,3-phenylene and the like and $R_1$—Si—(OR$_3$)$_m$; where $R_1$, $R_3$ and m are the same as in Formula (I) above;

$R_5$ represents any of formulae (6) or (7)

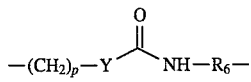
(6)

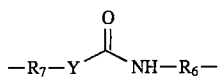
(7)

where p is an integer from 2 to 25; Y is any of O, S or N; and $R_6$ and $R_7$ are as defined in Formula (III).

The urea derivatives of Formula (5) are formed by reacting an organic polyisocyanate compound with a secondary amine or primary amine. Of these polyisocyanates, diisocyanates are preferred due to cost and availability. Typical diisocyanates which may be used in synthesis of the urea derivatives employed to provide the resin oligomers of the invention include but are not limited to 1,5-naphthalene diisocyanate; cumene-2,4-diisocyanate; 4-methoxy-1,3-phenylene diisocyanate; 4-chloro-1,3-phenylene diisocyanate; 4-bromo-1,3-phenylene diisocyanate; 4-ethoxy-1,3-phenylene diisocyanate and 2,4'-diisocyanato diphenyl ether.

Useful secondary amines which may be employed to react with the above diisocyanates to form the urea derivatives (5) employed to produce the resin oligomers of Formula (III) include amino compounds having the formula (8)

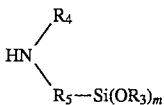
(8)

where m=1–3, $R_3$ may be any one of linear or branched primary, secondary or tertiary alkyl radicals having 2 to 4 carbon atoms. Examples of alkyl radicals which may be employed include $C_4H_8$, $C_2H_4$, $C_3H_6$; $R_3$ is a linear or branched primary, secondary or tertiary alkyl radical which has 2 to 4 carbon atoms. $R_4$ is any of $R_1$, as defined above in Formula (I), $C_1$–$C_{25}$ branched or straight alkyl such as methyl, ethyl, propyl, butyl, pentyl, hexyl, heptyl, octyl, 2-dodecyl, 3-dodecyl, 2,3-dimethyl decyl, 2-ethyl decyl, 2,5-dimethyldecyl, n-penta decyl, 2-hexa decyl, n-hepta decyl, 2-hepta decyl, 2 methyl-2-hepta decyl, 2-ethyl-2-hexa decyl, n-nona decyl, n-eicosyl, sec-eicosyl, n-hexaeicosyl, and n-docosyl; aryl such as phenyl, biphenyl, 1,5-naphthalene, anthracene, and the like; substituted aryl such as 4-methoxy-1,3-phenylene, 4-chloro- 1,3-phenylene, 4-bromo-1,3-phenylene and the like; and $R_1$—Si—$(OR_3)_m$ where m is an integer from 1–3; $R_5$ is any of formulae (6) or (7), and $R_6$ and $R_7$ are the same as are defined in Formula (III).

Typically, 1–6 moles of the above diisocyanates can be reacted with 1–3 moles of the above amines to provide urea derivatives of formula (5) which may be employed to provide oligomers of Formula (III).

The urea derivatives of Formula (5) produced by reaction of diisocyanate and amine is reacted with an acrylate substituted diol of Formula (3) to provide the resin oligomers of Formula (III) described above.

Generally, when producing a composition of Formula (III) where X is N, a polyisocyanate is reacted with an amine to form a urea derivative which is subsequently reacted with a polyol. The amine can be a secondary amine containing an alkoxy silane substitituent. The polyol can be a diol substituted with acrylate moieties and methacrylate moieties. In the manufacture of oligomers of Formula (III) where X is oxygen, the polyol is reacted with a polyisocyanate and an alcohol, instead of a urea derivative. In the manufacture of oligomers of Formula (III) where X is sulfur, the polyol is reacted with a thiol instead of a urea derivative.

Oligomers of Formula (III) where X is oxygen thus can be formed by reacting a polyol, such as an acrylate substituted diol of formula (3), with a polyisocyanate and an alcohol having a carbamate substituent. Typically 1–3 moles of the alcohol are reacted with 1–3 moles of the polyisocyanate and 2–6 moles of the acrylate substituted diol to form an oligomer according to Formula (III) wherein X is oxygen. This reaction can be accomplished by reacting a polyol and a polyisocyanate to form a first intermediate, and then reacting an alcohol having a carbamate substituent and a polyisocyanate to form a second intermediate. The first and second intermediates can then be reacted to form an oligomer according to formula (III).

A second method of providing oligomers of formula (III) where X is oxygen is to react a polyol with a diisocyanate compound and an alcohol having a carbamate substituent to form an oligomer according to formula (III). Polyols useful for this reaction include acrylate substituted diols of formula (3). Because of their relatively low cost and availability, diisocyanate are preferred as the polyisocyantes for producing oligomers of Formula (III) wherein X is oxygen. Useful diisocyanate include but are not limited to 4,4'-diisocyanato diphenyl; 2,4-diisocyanatostilbene, 3,3'-dimethoxy-4,4'-diisocyanato phenyl methane; 3,3'-dimethoxy-4,4'-diisocyanato diphenyl; 1,4-anthracene diisocyanate; 2,5-fluorene diisocyanate; 1,8-naphthalene diisocyanate, 2,6-diisocyanato benzfuran; amyl benzene-2,4-diisocyanate; polymethylene diisocyanates such as tetramethylene diisocyanate, pentamethylene diisocyanate, hexamethylene diisocyanate and the like; cycloaklylene diisocyanates such as cyclohexylene-1,4-diisocyanate; 4,4'-methylene bis(cyclohexyl isocyanate); isophorone diisocyanate; hetero chain diisocyanates such as OCN—R—$[(OCCH_2)_m$—$O]_n$R—NCO wherein R is as defined above in Formula (I), m=2–10, and n=1–10.

Alcohols useful in this method of synthesis have the general formula (9)

(9)

wherein $R_3$ and $R_5$ are defined as above. An example of a suitable alcohol is 1,3-dimethyl-3-hydroxy,butyl N-(3-triethoxysilyl propyl) carbamate.

When X is sulfur in the oligomers of formula (III), synthesis can be accomplished by reacting 1–3 moles of thiol with 2–6 moles of a polyisocyanate and 1–3 moles of an acrylate substituted diol according to formula (3) to form an oligomer according to Formula (III)

Suitable poly-isocyanates are the same as those useful in the synthesis of oligomers of Formula (III) wherein X is oxygen. Disocyantes are preferred. Suitable disocyantes include but are not limited to 2,4-dimethyl-1,3-phenylene diisocyanate; 4,4'-diisocyanato diphenyl ether; benzidine diisocyanate; 4,6-dimethyl-1,3-phenylene diisocyanate; 9,10-anthracene diisocyanate; 4,4'-diisocyanato diphenyl; 2,4-diisocyanatostilbene, 3,3'-dimethoxy-4,4'-diisocyanato phenyl methane; 3,3'-dimethoxy-4,4'-diisocyanato diphenyl; 1,4-anthracene diisocyanate; 2,5-fluorene diisocyanate; 1,8-naphthalene diisocyanate, 2,6-diisocyanato benzfuran; amyl benzene- 2,4-diisocyanate; polymethylene diisocyanates such as tetramethylene diisocyanate, pentamethylene-diisocyanate, hexamethylene diisocyanate and the like; cycloaklylene diisocyanates such as cyclohexylene- 1,4-diisocyanate; 4,4'-methylene bis(cyclohexyl isocyanate); isophorone diisocyanate; hetero chain diisocyanates such as OCN—R—$[(OCCH_2)_m$—$O]_n$R—NCO wherein R is as defined above, m=2–10, and n=1–10.

Thiols useful in the synthesis of compounds of formula (III) where X is sulfur have the general formula $$(R_3O)_m\text{—Si—}R_5\text{—SH} \tag{10}$$

where $R_3$, $R_5$, $R_6$ and $R_7$ are as defined above in Formula (III). An example of a suitable thiol is 3-mercapto propyl-N-(3-triethoxysilyl propyl) thio carbamate.

The resin oligomers of the invention can be diluted with reactive acrylate or methacrylate monomers to provide the desired conformal, dual curing resin formulations. Catalysts for moisture curing and photoinitiators for increasing the rate of UV curing may be included in the resin formulation. Surfactants for flow and coating characteristics also may be included.

The conformal resin compositions of the invention may include additional additives such as antioxidants, inhibitors, activators, fillers, pigments, dyes, antistatic agents, flame-retardant agents, thickeners, thixotropic agents, surface-active agents, viscosity modifiers, plasticizers and the like. Such additives generally are preblended prior to formulating with the conformal resin compositions. The additional additives may be present in amounts up to 8 parts or more per 92 parts of curable resin composition by weight, preferably 1 to 8 parts by weight. The type and amount of additive must be selected with care so that the final composition remains radiation curable under conditions of exposure. Useful surfactants include non-ionic types such as Fluorad brand (3M) and Igepals from GAF.

Useful reactive acrylate or methacrylate employed diluents correspond to formula (11)

$$\underset{\underset{R_8}{|}}{CH_2}=\underset{}{C}-\underset{\underset{O}{||}}{C}-R_9 \tag{11}$$

wherein $R_8$ is a radical selected from the group of hydrogen and lower alkyl of 1 to 4 carbon atoms; $R_9$ is an organic radical of $C_8$–$C_{20}$ containing an other acrylate group or a heterosubstituted alkyl radical such as tetrahydrofuryl; 2-methoxy-ethyl; 2-ethoxyethyl; 2-(2-ethoxy-ethoxy) and ethyl; 2-phenoxy ethyl; glycidyl; triethylene glycol and ethylene glycol. Preferably, $R_9$ is an aliphatic or substituted aliphatic carbon ring structure such as dicyclopentyloxyethyl. Other allylic-bond containing carbon ring structures such as dicyclopentenyl which is given as exemplary also may be employed. Additional examples of acrylate or methacrylate monomers for diluting the resin oligomer include but not limited to bisphenol-A diacrylate; bisphenol-A dimethacrylate; isobornyl acrylate, diethylene glycol diacrylate; diethylene glycol dimethacrylate; ethylhexyl acrylate; ethylhexyl methacrylate; 1,6-hexanediol diacrylate; 1,6-hexanediol dimethacrylate; neopentyl glycol diacrylate; neopentyl glycol dimethacrylate; pentaerythritol tetraacrylate; pentaerythritol triacrylate; polyethylene glycol diacrylate; polyethylene glycol dimethacrylate; tetraethylene glycol diacrylate; tetraethylene glycol dimethacrylate; triethylene glycol diacrylate; triethylene glycol dimethacrylate; trimethylolpropane triacrylate; trimethylolpropane trimethacrylate.

Vinyl ether monomers can also be employed as diluents. Examples of these diluents include but are not limited to tetraethylene glycol divinylether, 1,4-cyclohexanedimethanol divinyl ether, 2-ethylhexylvinylether, dodecylvinylether, trivinyl ether of trimethylolethane, hydroxybutyl vinyl ether and divinyl ether of 1,4-butanediol.

The amount of monomer diluent added can vary between wide limits. Generally, 10 to 60% by weight of the composition, preferably 40 to 60% by weight is added. The reaction mixture further may include titanates and photoinitiators as catalysts for moisture curing and free radical and cationic polymerization, respectively.

As indicated, photoinitiators may be included with the conformal resin formulations to assist in UV curing. Various photoinitiators are operable and well known to those skilled in the art. Examples of photoinitiators include, but are not limited to, benzophenone, acetophenone, acenaphthenequinone, methyl ethyl ketone, valerophenone, hexanophenone, α-phenylbutyrophenone, p-morpholinopropiophenone, dibenzosuberone, 4-morpholinobenzophenone, 4-morpholinodeoxybenzoin, p-diacetylbenzene, 4-aminobenzophenone, 4'-methoxyacetophenone, benzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,4-triacetylbenzene, thioxanthen-9-one, xanthene-9-one, benzoin isobutyl ether, chloroxanthone, benzoin tetrahydropyranyl ether, benzoin methyl ether, benzoin isopropyl ether, 7-H-benzoin methyl ether, benzoin isopropyl ether, ben[de]anthracene-7-one, 1-naphthaldehyde, 4,4'-bis(dimethylamino)benzophenone, fluorene-9-one, 1'-acetonaphthone, 2'acetonaphthone, o-methoxybenzophenone, triphenylphosphine, tri-o-tolylphosphine, benz[a]anthracene 7,12 dione, 2,2-diethoxyacetophenone, 2,2-dimethoxy-2-phenylacetophenone and 2,3-butanedione, which serve to give greatly reduced exposure times. Photoinitiators, such as those above, when used in conjunction with energetic radiation, yield very rapid time cycles. The photoinitiators are usually added in an amount ranging from 2 to 8% by weight of the photocurable composition.

The resin formulation may be cured by either UV radiation or high energy ionizing radiation. Secondary curing of portions of the resin formulation not exposed to the radiation may be cured by exposure to moisture. The UV radiation can be obtained from sunlight or special light sources which emit significant amounts of U.V. light having a wavelength in the range of about 2000 to about 4000 Angstrom units. Any type of actinic light from any source may be used in carrying out the method of this invention. For liquid photocurable compositions, it is preferred that the light emanate from a point source or in the form of parallel rays. Divergent beams, are however, also operable as a source of actinic light.

A class of actinic light useful herein is ultraviolet light, as well as other forms of actinic radiation which are normally found in radiation emitted from the sun or from artificial sources such as Type RS Sunlamps, carbon arc lamps, xenon arc lamps, mercury vapor lamps, tungsten halide lamps and the like. Ultraviolet radiation may be used most efficiently if the photocurable acrylate composition contains a suitable photo-curing rate accelerator. Curing periods may be adjusted to proper choice of ultraviolet source, photocuring rate accelerator and concentration thereof, temperature and the oligomer and monomer diluents. Curing periods of less than about 1 second duration are possible, especially in thin film application such as desired, for example, in coatings, adhesives and photoimaged surfaces. The preferred free radical generator for the curing reaction is actinic radiation, suitably in the wavelength of about 2000 to 7500 Å, preferably from 2000 to 4000 Å.

The radiation curable compositions of the invention also can be primarily cured by high energy ionizing irradiation such as by high energy particle irradiation, gamma-rays or X-rays. Irradiation employing high energy particles includes use of positive ions, (e.g., protons, alpha particles and deuterons), electrons and neutrons. The charged particles may be accelerated to high energies by means of various voltage gradient mechanisms such as a Van de Graaf generator, a cyclotron, a Cockroft Walton accelerator, a resonant cavity accelerator, a betatron, a G.E. resonant transformer, a synchrotron or the like. Furthermore, particle irradiation may also be supplied from radioactive isotopes or an atomic pile. Gamma rays or X-rays may be obtained from radioisotopes (e.g., cobalt 60) or by particle bombardment or suitable target material (e.g., high energy electrons on a gold metal target).

Conventional polymerization inhibitors or retarders may be added to the resin formulation to stabilize the components or curable compositions so as to prevent premature onset of curing during storage. Examples of inhibitors and retarders may include hydroquinone; p-tert-butyl catechol; 2,6-di-tert-butyl-p-methylphenol; phenothiazine; N-phenyl-2-naphthylamine; phosphorous acid; pyrogallol and the like.

Inhibitors which are preferred include hydroquinones, benzoquinones, naphthoquinones, phenanthraquinones, anthraquinones, and substituted compounds of any of the foregoing. Additionally, various phenols can be employed as inhibitors, the preferred one being 1,6-di-tert-butyl-4-methyl phenol.

The following examples are set out to explain, but expressly not limit, the instant invention. Unless otherwise specified, all parts and percentages are by weight.

EXAMPLE 1

45.1 g of commercially available (Union Carbide) 3-trimethoxysilyl di-n-propyl amine is added dropwise to a 3-necked flask containing 34.5 g dicyclohexylmethane- 4,4'-diisocyanate and 0.3 g COTIN 200 a urethane catalyst available (Caschem Inc.). The reaction exotherms to 70° C. and is continued at 90°–95° for 1–2 hours for completion of reaction. To the reaction product is added 32.6 g of 3-isocyanatopropyl triethoxysilane available from Union Carbide, preferably all at once, along with 0.16 g. hydroquinone monomethylether (MEHQ). Started bubbling dry air (grade O) through the reaction mixture and added 53.3 g 1,4-butanediol di(3-acryloxy-2-hydroxypropyl) ether, all at once. The reaction temperature is raised to 80°–85° C. and maintained at this temperature until complete as shown by the disappearance of the NCO band by infra-red spectroscopy. The resulting resin oligomer has the following Formula (Ia):

EXAMPLE 2

A dual curable resin formulation containing the resin oligomer of Formula (Ia) is made up as follows: 72.2 g of the oligomer of Formula (Ia) of Example 1 is admixed with reactive diluent of 13.8 g isobornyl acrylate available from Sartomer Co., Exton, Pa., a reactive diluent of 5.0 g. Ebecryl 110 available from Radcure Specialties Inc., a reactive diluent of 5.0 g γ-Methacryloxypropyl trimethoxysilane available from Union Carbide under the tradename A-174, a moisture cure catalyst of 1.0 g Tyzor TBT available from DuPont, and 3.0 g Irgacure 184 photoinitiator available from Ciba-Geigy. The mixture is heated to 60° C., with stirring, in a flask in total darkness and protected from moisture until a homogenous mixture is formed. The resulting solution is stored in an amber container to protect the contents from light. This formulation, referred to as Resin Formulation (A), is cured by exposing it to a 400 watts mercury vapor lamp generating (200–400 nm) for 10–20 seconds. The resulting polymer film is tested for mechanical and electrical properties according to ASTM methods D142, D150, and D257. The results are listed in Table I.

EXAMPLE 3

90.1 g of commercially available 3-trimethoxysilyl di-n-propyl amine available from (Union Carbide) is added dropwise to a 3-neck flask containing 44.4 g of 1,6-diisocyanatohexane and 0.2 g COTIN 200®, dibutyl tin dilacrylate from Caschem Co. The temperature of the reaction mixture is maintained at 90°–95° C. for 1–2 hours. The reaction mixture is cooled at 70° C., whereafter 0 18 g hydroquinone monoemthylether (MEHQ) is added. Passage of dry air (grade O) through the reaction cycle is initiated and 50 g of 1,4-butanediol di(3-acryloxy-2-hydroxypropyl) ether is added all at once. The reaction temperature is raised to 80°–85° C. and maintained at that temperature until complete as shown by the disappearance of the NCO band by IR spectroscopy. The resulting resin oligomer product of Formula (IIa) is produced:

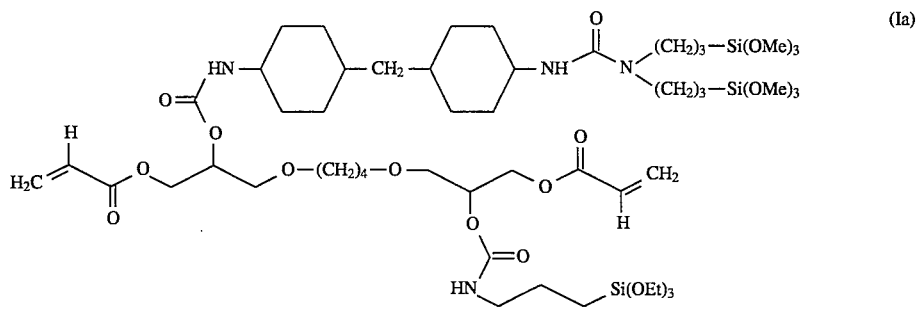

(Ia)

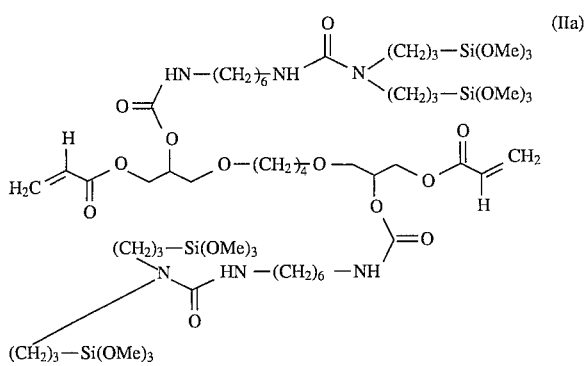

(IIa)

EXAMPLE 4

70 g of the Oligomer of Formula (IIa) is admixed with 17.5 g isobornyl acrylate, 6.25 g Methacryloxyproply trimethoxysilane available from Union Carbide under the tradename A-174, 6.25 g Ebecryl 110, 1.0 g. Tyzor TBT and 3.0 g Irgacure 184. The mixture is warmed to 60° C., with mixing, until a homogenous solution is produced. The resulting resin, referred to as Resin Formulation (B), is cured by UV radiation as described in example 2. The results of the tests performed on the coating formulation produced are given in Table I.

EXAMPLE 5

93.6 g of commercially available 3-trimethoxysilyl di-n-propyl amine is added, dropwise, to a three necked flask containing 71.8 g dicyclohexylmethane- 4,4'-diisocyanate and 0.36 g COTIN 200®. The temperature of the reaction mixture is raised to 90°–95° C. and maintained at this temperature for 1–2 hours. The reaction mixture is cooled to 70° C. whereafter 0.21 g MEHQ is added. Dry air (grade O) then is bubbled through the reaction mixture during the reaction cycle, and 51 g of 1,4-butanediol di(3-acryloxy-2-hydroxy propyl) ether is added all at once. The reaction temperature is raised to 80°–85° C. and maintained at this temperature until complete as shown by the disappearance of the NCO band by IR spectroscopy. The resulting resin oligomer product has the structure below:

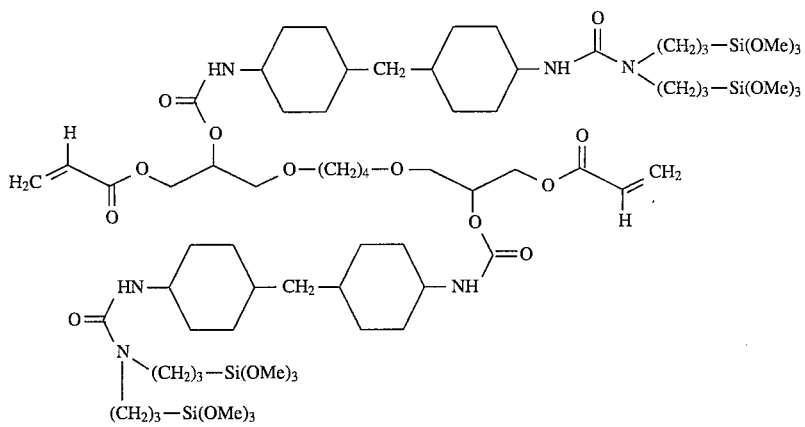

EXAMPLE 6

58.4 g of the Oligomer of example 5 is admixed with 30.8 g isobornyl acrylate, 10.8 g A-174, 1.0 g Tyzor TBT and 3.0 g Irgacure 184. The mixture is warmed to 60° C., with stirring, until a homogenous solution is produced. The resulting Resin Formulation (C) is cured by UV radiation as described in example 2. The results of the tests conducted on the polymer obtained from Formulation C are tabulated in Table I.

TABLE I

| Resin Formulation | A | B | C |
| --- | --- | --- | --- |
| Volume Resistivity ohm -cm × 10¹² | 0.31 | 4.30 | 4.90 |
| Tensile Strength psi | 257.00 | 421.00 | 474.00 |
| Dielectric Constant at 1 Khz | 4.15 | 4.83 | 3.93 |
| Dissipation Factor | 0.093 | 0.16 | 0.067 |
| % Elongation | 10.80 | 10.30 | 9.80 |
| Modulus, psi | 6872.00 | 5440.00 | 8971.00 |
| Durometer, Shore A | 90.00 | 93.00 | 95.00 |

EXAMPLE 7

50.0 g of N-methylaminopropyl trimethoxysilane (commercially available from Huls America Inc.) is added dropwise to a 4-necked flask containing 92.6 g of Mondur 744 available from Miles, 0.34 g of Cotin® 200, (a urethane catalyst available from Caschem Inc.), 0.3 g of hydroquinone monomethylether (MEHQ), 108.19 g of 2-Phenoxyethyl acrylate (Commercially available from Sartomer Co., Exton, Pa. as Sartomer 340), and 72.0 g of isodecyl acrylate (Commercially available from Sautomer Co., Exton, Pa. as Sartomer 395). The addition rate of the N-methylaminopropyl trimethoxysilane is such that the reaction temperature does not rise above 25°–30° C. After the completion of addition of the N-methylaminopropyl trimethoxysilane, the reaction temperature is raised to about 80°–85° C. and maintained in this range for about 1 hour. Then 44.75 g of 1,4-butanediol di(3-acryloxy-2-hydroxypropyl) ether is added all at once. The reaction temperature is raised to about 80°–85° C. and maintained at this temperature until the reaction is complete as shown by the disappearance of the NCO band by infrared spectroscopy (usually about 2 hours). To the resin formed is added 9.86 g of Irgacure 184 (a photoinitiator commercially available from Ciba-Geigy), 9.86 g of Esacure KB-1 (a photoinitiator available from Sartomer Co.), 0.15 g Uvitex OB (a fluorescent indicator available from Ciba-Geigy), 1.23 g Fluorad FC-430 (a surfactant available from 3M Co.), a reactive diluent of 73.95 g γ-methacryloxypropyltrimethoxysilane (available from Union Carbide under the tradename A-174), and 0.2 g MEHQ at 60°–65° C. The reaction mixture is stirred for 15 minutes and cooled to a temperature of about 30°–35° C. 29.6 g acrylic acid is then added as a reactive diluent and the resulting mixture is stirred for 15 minutes. The final product is a compound of Formula (III).

EXAMPLE 8

153.3 g of N-phenylaminopropyl trimethoxysilane (commercially available from Union Carbide under the tradename Y-9669) is added dropwise to a 4-necked flask containing 214.8 g of Mondur 744 available from Miles, 0.96 g of Cotin® 200 a urethane catalyst available from Caschem Inc., 0.81 g of hydroquinone monomethylether (MEHQ), 312.0 g of 2-Phenoxyethyl acrylate (available from Sartomer Co., Exton, Pa., under the tradename Sartomer 340) and 208.28 g of isodecyl acrylate (available from Sartomer Co. under the tradename Sartomer 395). The addition rate of N-phenylaminopropyl trimethoxysilane is such that the reaction temperature does not rise above 25°–30° C. After all of the amine has been added the reaction tempature is raised to 80°–85° C. and maintained at this level for 1 hour. Then 105.0 g of 1,4-butanediol di(3-acryloxy-2-hydroxypropyl) ether is added all at once. The reaction temperature is raised to 80°–85° and maintained at this temperature until the reaction is completed as shown by the disappearance of the NCO band by infrared spectroscopy (usually 2 hours). To the above resin is added 27.3 g of Irgacure 184 (a photoinitiator available from Ciba-Geigy), 27.3 g of Esacure KB-1 (a photoinitiator available from Sartomer Co.), 0.69 g Uvitex OB (a fluorescent indicator available from Ciba-Geigy), 3.39 g Fluorad FC-430 (a surfactant available from 3M Co.), a reactive diluent of 202.8 g τ-methacryloxypropyl trimethoxy-silane (available from Union Carbide under the tradename A-174). After 15 minutes, the reaction mixture is cooled to 30°–35° C. and then 81.0 g acrylic acid reactive diluent is added and stirred for 15 minutes. Then 13.52 g of Tyzor TBT is added and the reaction mixture is stirred for another 15 minutes. The product is stored in an amber container. The final product is a compound having structural formula (III).

EXAMPLE 9

123.7 g of 3-isocyanatopropyltriethoxysilane (commercially available from Union Carbide under the tradename A-1310) is added dropwise to a 500 mL 4-necked flask containing 59.1 g of 2-methyl-2,4-pentanediol (hexylene glycol) (available from Union Carbide), 0.3 g of Cotin® 200 (a urethane catalyst available from Caschem Inc.), over 5 minutes. The reaction is exothermic and the temperature rises to about 70° C. The reaction mixture is maintained at 70° C. until the reaction is complete as indicated by the disappearance of the NCO band as indicated by infrared spectroscopy. The alcohol produced has the structure

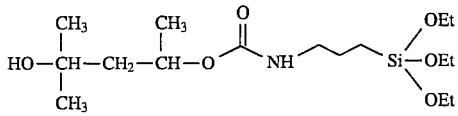

This alcohol is used for preparation of the dual curing resin of Example 10.

EXAMPLE 10

36.0 g of 1,4-butanediol di(3-acryloxy-2-hydroxypropyl) ether is added all at once to a 3-necked flask containing 71.6 g of Mondur 744, 0.35 g COTIN® 200, 0.38 g MEHQ, 115.7 g of Sartomer 340 and 77.18 g Sartomer 395. The reaction temperature is raised to 80°–85° C. and maintained at that level for 1½ hours. 74.2 g of the alcohol produced in Example 9 is then added to the reaction mixture all at once. The temperature is maintained at 80°–85° C. until the reaction is complete as shown by the disappearance of the NCO band by infrared spectroscopy. 10.3 g of Irgacure 184, 10.3 g of Esacure KB-1, 0.13 g MEHQ, 0.26 g Uvitex OB, 1.3 g Fluorad FC-430, and 77.1 g of A-174 are added to the three necked flask and the reaction mixture is stirred for 15 minutes. The reaction mixture is cooled to 30° C. and 30.9 g acrylic acid and 10.3 g of Tyzor TBT is added. The reaction mixture is stirred for 15 minutes and the product is stored in amber or opaque containers. The resulting Oligomer has the structure below:

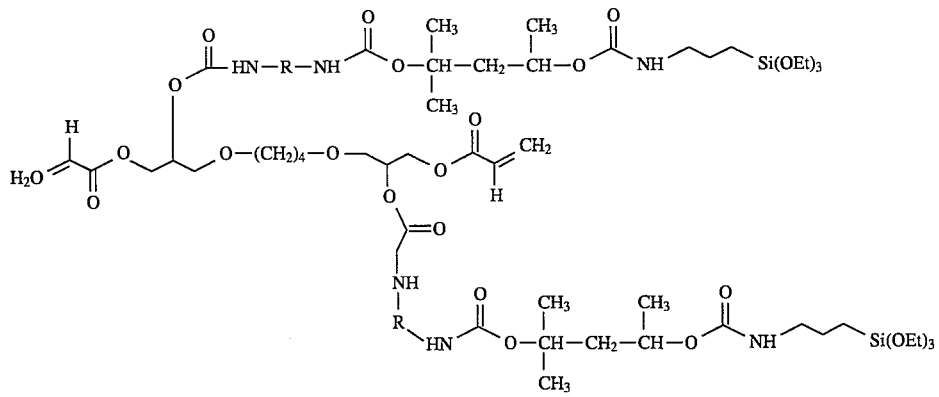

EXAMPLE 11

123.7 g of 3-isocyanatopropyltriethoxysilane (commercially available from Union Carbide under the tradename A-1310) is added dropwise to a 500 mL 4-necked flask containing 76.0 g of 1,3 di mercapto propane, 0.3 g of Cotin® 200 (a urethane catalyst available from Caschem Inc.), over 5 minutes. The reaction mixture is maintained at 70° C. until the reaction is complete as indicated by the disappearance of the NCO band as indicated by infrared spectroscopy. The thiol so produced is stored for later use.

36.0 g of 1,4-butanediol di(3-acryloxy-2-hydroxypropyl) ether is added all at once to a 3-necked flask containing 71.6 g of Mondur 744, 0.35 g COTIN® 200, 0.38 g MEHQ, 115.7 g of Sartomer 340 and 77.18 g Sartomer 395. The reaction temperature is raised to 80°–85° C. and maintained at that level for 1½ hours. 96.5 g of the thiol previously produced is then added to the reaction mixture all at once. The temperature is maintained at 80°–85° C. until the reaction is complete as shown by the disappearance of the NCO band by infrared spectroscopy. 10.3 g of Irgacure 184, 10.3 g of Esacure KB-1, 0.13 g MEHQ, 0.26 g Uvitech OB, 1.3 g Fluorad FC-430, and 77.1 g of A-174 are added to the three necked flask and the reaction mixture is stirred for 15 minutes. The reaction mixture is cooled to 30° C. and 30.9 g acrylic acid and 10.3 g of Tyzor TBT are added. The reaction mixture is stirred for 15 minutes and the product is stored in amber or opaque containers.

As will be appreciated, the foregoing invention provides novel and improved coating systems for conformal coating printing circuit boards assemblies and the like by any convenient manner, for instance a spraying, brushing, dripping, rolling, dipping, etc. Moreover, the coating systems cure through dual mechanisms including UV cure which permits fast fixture cure thereby achieving almost immediate dry-to-the touch curing. However, unlike conventional UV cured products, the coating systems of the present invention cures the resin which does not "see" the UV radiation due to their built in secondary moisture cure mechanism. Moreover, the cured coatings have excellent adherence to plastics, metal, glass and wood, good abrasion resistance, and are hydrolytically stable and resistant to thermal cycling. The coatings also are repairable, i.e., can be removed by selective solvents such as tetrahydrofuran, and then replaced by brush or spray, and UV cured.

The invention has been described particularly with applications to conformal coating circuit board assemblies. However, one skilled in the art would appreciate that the coating systems may be applied to other electrical electronic components such as transformers or the like. Moreover, the coating composition is not limited to the use in the electronics field but may be employed in any industrial area where conformal protective coating is desired.

What is claimed is:

1. An oligomer according to formula (III) comprising $$\text{(III)}$$

[structure of formula (III) shown]

where X is selected from the group consisting of O, N and S, with the proviso that when X is either O or S, $R_4$ is not present;

R is selected from the group consisting of aryl, alkoxy substituted aryl, aryl substituted alkyl, aryl ether, cycloalkyl substituted alkyl, halo-substituted aryl, alkyl substituted aryl alkyl, alkoxy substituted aryl and (—CH$_2$)p— where p is an integer from 4 to 6;

$R_2$ is selected from the group consisting of H, —CH$_3$ and —C$_2$H$_5$;

$R_3$ is selected from the group consisting of —CH$_3$, —C$_2$H$_5$, —R$^1$—CO—(CH$_2$)$_Q$—O$_t$—R$_1$ where R$_1$=R as defined above, Q is an integer from 2 to 10 and t is an integer from 1 to 10;

$R_4$ is selected from the group consisting of $R_1$, $C_1$–$C_{25}$ branched or straight alkyl, aryl, substituted aryl and $R_1$—Si—(OR$_3$)$_m$;

$R_5$ is selected from the group consisting of $$-(CH_2)_p-Y-\underset{\underset{O}{\|}}{C}-NH-R_6-$$

and, $$-R_7-Y-\underset{\underset{O}{\|}}{C}-NH-R_6-$$

where p is an integer from 2 to 25; Y is selected from the group consisting of O, S or N;

$R_6$ is selected from the group consisting of $C_1$–$C_{25}$ straight and branched alkyl;

$R_7$ is selected from the group consisting of $C_1$–$C_{25}$ branched or straight alkyl, aryl and substituted aryl;

n is an integer from 2 to 20; and m is an integer from 1–3.

2. The oligomer of claim 1 wherein:

$R_2$ represents H, —CH$_3$, —C$_2$H$_5$;

$R_3$ represents —CH$_3$, —C$_2$H$_5$, —C$_3$H$_7$;

$R_5$ represents $$-(CH_2)_p-Y-\underset{\underset{O}{\|}}{C}-NH-R_6-$$

wherein $R_6$ represents $C_1$–$C_{25}$ straight or branched alkyl; Y is N, O, or S and p is an integer from 2–25.

3. The oligomer of claim 1 wherein

R represents dicyclohexylmethane, hexamethylene;

$R_2$ represents H, CH$_3$; and n=4, 6

$R_5$ represents $$-\underset{\underset{CH_3}{|}}{CH}-CH_2-\underset{\underset{CH_3}{|}}{CH}-O-\underset{\underset{O}{\|}}{C}-NH-CH_2CH_2CH_2-Si\underset{\diagdown OEt}{\overset{\diagup OEt}{-OEt}}$$

4. The oligomer of claim 1 wherein

R represents dicyclohexylmethane;

$R_2$ represents H, and n=6

$R_5$ represents $$-\underset{\underset{CH_3}{|}}{CH}-CH_2-\underset{\underset{CH_3}{|}}{CH}-O-\underset{\underset{O}{\|}}{C}-NH-CH_2CH_2CH_2-Si\underset{\diagdown OEt}{\overset{\diagup OEt}{-OEt}}$$

5. A method of making an oligomer of the structure of Formula (III) of claim 1 wherein an alcohol is reacted with a polyisocyanate and an acrylate substituted diol.

6. The process of claim 5 wherein the thiol has the general formula $$(R_3O)_m-Si-R_5-SH$$

where $R_3$ is selected from the group consisting of —CH$_3$, —C$_2$H$_5$, —C$_3$H$_7$;

$R_5$ is selected from the group consisting of

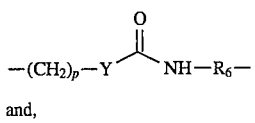

and,

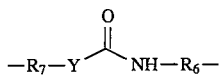

where p is an integer from 2 to 25;

Y is selected from the group consisting of O, S or N;

$R_6$ is selected from the group consisting of $C_1$–$C_{25}$ straight and branched alkyl;

$R_7$ is selected from the group consisting of $C_1$–$C_{25}$ branched or straight alkyl, aryl and substituted aryl;

n is an integer from 2 to 20; and m is an integer from 1–3.

7. The process of claim 5 wherein the alcohol has the general formula $$(R_3O)_m\text{—Si—}R_5\text{—OH}$$

where $R_3$ is selected from the group consisting of —$CH_3$, —$C_2H_5$, and —$C_3H_7$;

$R_5$ is selected from the group consisting of

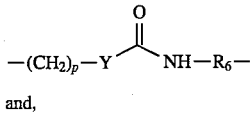

and,

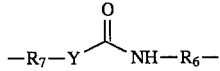

where p is an integer from 2 to 25;

Y is selected from the group consisting of O, S or N;

$R_6$ is selected from the group consisting of $C_1$–$C_{25}$ straight and branched alkyl;

$R_7$ is selected from the group consisting of $C_1$–$C_{25}$ branched or straight alkyl, aryl and substituted aryl.

8. The method according to claim 7 where $R_3$ of the alcohol is ethyl.

9. The method according to claim 6 where $R_5$ of the thiol is

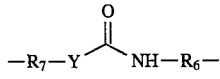

10. A method of making an oligomer of Formula (III) claim 1 wherein a thiol is reacted with a polyisocyanate and an acrylate substituted diol.

11. A method for making the oligomer of the structure of Formula (III) of claim 1 which comprises reacting a polyol with a urea derivative formed from the reaction product of an organic polyisocyanate and an alkoxy substituted amine.

12. The method of claim 11 wherein the polyol is substituted with acrylate or methacrylate moieties.

13. The method of claim 11 wherein the urea derivative has formula (5);

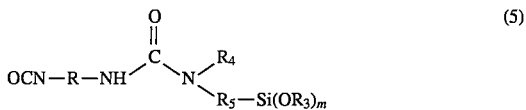     (5)

where

R represents $(CH)_{2n}$, n=1–6; substituted phenyl, cyclohexyl;

$R_3$ represents $C_2$–$C_4$ alkyl;

$R_4$ represents $C_1$–$C_{25}$ branched or straight alkyl, aryl, substituted aryl or $R_6$—Si—$(OR_3)_m$ $R_5$ is selected from the group consisting of

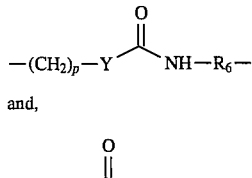

and,

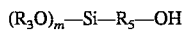

where p is an integer from 2 to 25;

Y is selected from the group consisting of O, S or N;

$R_6$ is selected from the group consisting of $C_1$–$C_{25}$ straight and branched alkyl;

$R_7$ is selected from the group consisting of $C_1$–$C_{25}$ branched or straight alkyl, aryl and substituted aryl.

14. The method of claim 13 wherein, in the urea derivative R represents dicyclohexylmethane or hexamethylene; $R_5$ is as defined in claim 13;

$R_7$ is selected from the group consisting of $C_1$–$C_{25}$ branched or straight alkyl, aryl and substituted aryl.

15. The method of claim 13 wherein, in the urea derivative, R represents dicyclohexylmethane and $R_5$ represents

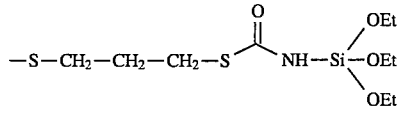

* * * * *